United States Patent [19]

Keegan

[11] Patent Number: 4,495,314

[45] Date of Patent: Jan. 22, 1985

[54] DENTURE ADHESIVE CREAMS WITH IMPROVED EXTRUDABILITY

[75] Inventor: James J. Keegan, Bloomfield, N.J.

[73] Assignee: Warner-Lambert Company, Morris Plains, N.J.

[21] Appl. No.: 323,508

[22] Filed: Nov. 23, 1981

[51] Int. Cl.$^3$ .............................................. A61K 6/00
[52] U.S. Cl. ................................... 523/120; 433/180; 433/217
[58] Field of Search .................. 424/49; 433/180, 226, 433/217; 523/120

[56] References Cited

U.S. PATENT DOCUMENTS

| | | | |
|---|---|---|---|
| 3,215,599 | 11/1965 | Thau et al. | 167/63 |
| 3,833,518 | 9/1974 | Rubin et al. | 260/17 R |
| 3,913,259 | 10/1975 | Nishimura et al. | 43/114 |
| 3,963,832 | 6/1976 | Hashimoto | 424/56 |

OTHER PUBLICATIONS

Remington's Pharmaceutical Sciences 16th ed., pp. 1247, 1251 & 1253.

*Primary Examiner*—Paul Lieberman
*Assistant Examiner*—Amelia B. Yarbrough
*Attorney, Agent, or Firm*—Daniel A. Scola, Jr.; Gary M. Nath

[57] ABSTRACT

A vehicle useful in a denture adhesive composition, and the denture adhesive composition containing such vehicle is disclosed. The vehicle comprises a gel consisting essentially of a mineral oil, a polyethylene wax and sorbitan monostearate in an amount of from about 0.25% to about 2.25% by weight of the gel. Preferably, the sorbitan monostearate is present in an amount of from about 0.5% to about 2.0% by weight. The gel may optionally contain up to about 10% by weight of polyisobutylene. The addition of sorbitan monostearate within the above amounts appears to lower the viscosity of the gels, and provides notable improvements in extrudability when the vehicle is employed in denture adhesive compositions.

35 Claims, No Drawings

DENTURE ADHESIVE CREAMS WITH IMPROVED EXTRUDABILITY

BACKGROUND OF THE INVENTION

1. Field of the Invention

The present invention relates generally to denture adhesive compositions, and particularly to the vehicles or mobile phases thereof.

2. Description of the Prior Art

A variety of denture adhesives are known and commercially available in the form of creams, pastes and the like. These adhesive compositions generally comprise a gum phase, constituted by one or more non-toxic polymeric compositions, that are selected and formulated to provide the desirable adhesive properties between the denture and the adjacent structure in the user's mouth. The adhesive or gum phase usually comprises about 30 to 75% of the total adhesive composition, and a vehicle or mobile phase is included, comprising the remainder, for the purpose of providing flowability, smoothness of texture, and the other properties desirable to make the adhesive composition pleasant to utilize as well as effective. The mobile phase frequently consists of a mineral oil base that may be utilized alone, or together with other modifying ingredients such as flavors, colorants, extenders and other adjuvant materials. A particular mobile phase composition includes a mineral oil and a polyethylene wax possessing a molecular weight ranging from about 1500 to about 2500. This composition is disclosed in U.S. Pat. No. 3,215,599, to Thau,etal. Denture adhesives are generally disclosed in U.S. Pat. No. 3,833,518, to Rubin et al., and U.S. Pat. No. 3,003,988, to Germann et al., both disclosures of which are incorporated herein by reference.

With respect to the vehicle or mobile phase disclosed in Thau,etal., denture adhesive creams prepared with even this base or mobile phase, exhibit difficulty in extrudability, when the creams are packaged in tubes for commercial sale. In particular, excessive force is required to expel the cream from the tube, with the frequent result that either the tube will rupture over time, or the excessive force anticipated to expel the cream will result in the expulsion of more cream than is necessary for a particular application. In either event, the difficulty with extrudability of the denture adhesive creams has been a problem frequently reported by denture wearers.

Efforts have been made in the past to improve the extrudability of mobile phases or gels employed in ointments, and the like, without adversely affecting their consistency or texture. Such investigations were reported in Eros et al., "Investigation of the Rheological Characteristic of Ointment Gels Containing Emulsifiers and Emulsion-Type Ointments", Cosmetics & Toiletries, Volume 94, Pages 67–79, Allured Publishing Corp., New York, (1979). The authors incorporated emulsifiers including sorbitan monostearate into the gels at various concentrations, and examined the viscosity and spreadability of the resulting preparations. Sorbitan monostearate was found to exhibit improved spreadability, related to lowered viscosity, in amounts of from about 2.5% to 5.0% by weight. Outside of this range, the improved properties either were diminished or did not exist. In either event, a correlation between the presence of sorbitan monostearate and improvements in gel extrudability was not drawn, and was not apparent from the data gathered by the authors.

A need therefore exists for the development of a denture cream, and particularly, a mobile vehicle therefor, that offers improved extrudability, while retaining the desirable properties of gel-like viscosity and smooth coherent texture, necessary and desirable in denture adhesive preparations.

SUMMARY OF THE INVENTION

In accordance with the present invention, a denture adhesive composition possessing improved extrudability, while retaining the favorable properties of viscosity and texture, is disclosed which comprises a gum phase constituted by one or more adhesive compositions, and a mobile phase comprising a gel, the gel consisting essentially of mineral oil, a polyolefin wax, and from about 0.25% to about 2.25% by weight of the gel, of an extrusion aid comprising sorbitan monostearate. Preferably, the gel consists essentially of from about 75% to about 95% by weight of the mineral oil, and from about 0.5% to about 2.0% of the extrusion aid, with the balance comprising the polyolefin wax.

Preferably, the polyolefin wax comprises a polyethylene wax having a molecular weight ranging from about 1000 to about 500,000.

A further preferred denture adhesive composition includes a gel consisting essentially of from about 80% to about 90% by weight mineral oil, from about 0.5% to about 1.5% by weight of the extrusion aid, sorbitan monostearate, and the remainder, a polyethylene wax having a molecular weight within the aforenoted ranges.

The presence of the sorbitan monostearate within the aforementioned ranges unexpectedly improves viscosity and extrudability of the denture adhesive. Amounts of the extrusion aid falling outside the ranges specified herein show no improvement at all, and the resulting denture adhesive cream behaves as if the extrusion aid were absent entirely.

Denture adhesive creams and similar compositions prepared in accordance with the present invention, provide the desirable mechanical and aesthetic properties, at a minimum of cost, as the extrusion aid sorbitan monostearate is added in extremely small quantities, and is generally an inexpensive ingredient. Also, the processing associated with the preparation of the present compositions, is neither rigorous nor energy consumptive, and the phase may be prepared in the same manner already known in the art.

Accordingly, it is a principal object of the present invention to provide a denture adhesive composition that offers improved extrudability when the composition is packaged in a tube-like container for commercial purposes.

It is a further object of the present invention to provide a denture adhesive composition as aforesaid which exhibits its improved extrudability without adverse effect to consistency or adhesive properties.

It is a yet further object of the present invention to provide a carrier or vehicle for a variety of medicinal preparations, that combines the desired properties of consistency and flowability.

It is a still further object of the present invention to provide a carrier or vehicle for medicinal compositions, that is easily and inexpensively formulated.

Other objects and advantages will become apparent to those skilled in the art from a consideration of the ensuing description.

DETAILED DESCRIPTION

The present invention comprises a vehicle particularly suited for use in denture adhesive compositions, comprising a gel consisting essentially of a mineral oil, a polyolefin wax and sorbitan monostearate, present in an amount by weight of the gel, of from about 0.25% to about 2.25%. Optionally, the gel may contain up to about 10% by weight of an elastomeric material such as a polyisobutylene.

The mineral oils useful in the present invention may vary in viscosity, depending upon the thickening effect that is desired in the final product in which the gel is made a part. For example, an oil that may be utilized in the formation of gels having utility as vehicles or bases in salves, ointments, cosmetic creams and the like, comprises a highly refined white oil having a viscosity of about 50 to about 350 seconds at 38° C., and meeting the United States Pharmacopeia requirements as to taste, odor and acid tests. Such an oil, however, is merely exemplary of mineral oils useful in the present invention, and the invention is accordingly not limited thereto.

The polyolefin waxes or polymer waxes that are useful in the present invention, include the microcrystalline waxes, though other waxes such as paraffin wax, beeswax, shellac wax and the like may also be employed. Naturally, those polymer waxes having compatability with the petroleum oil utilized are preferred, and particularly, certain microcrystalline waxes comprising polyethylene waxes may be used. The polyethylene waxes utilized herein may vary in density, and may have molecular weights ranging from about 1,000, up to as high as 500,000, with a molecular weight ranging from 1,000 to 3,000, particularly preferred.

The extrusion aid useful in the present invention comprises sorbitan monostearate. The amount of sorbitan monostearate utilized may vary in its broadest aspect from about 0.25% to about 2.25% by weight of the gel or mobile phase. This broad range contrasts with the teachings of Eros et al., discussed earlier, as the authors found that amounts of the monostearate in excess of 2.5% by weight, and preferably from about 3% by weight to about 5% by weight, provided improved reduction in viscosity, which was postulated to yield a similarly favorable effect upon extrusion. The authors noted that this effect occurred unexpectedly within the aforementioned ranges, and was otherwise absent.

Accordingly, the present discovery is unexpected, as the extrusion aid, sorbitan monostearate, operates within a wholly different range, lying outside the range suggested by the authors of the Eros et al. article. The significance of this discovery, is that the benefits of improved extrusion are gained with a substantial reduction in the amount of extrusion aid that must be added. This is significant, as the addition of any ingredient, particularly one functioning as an emulsifier or surface active agent, in increased quantities, not only engenders additional costs in the preparation of the composition, but may adversely affect the properties of the resulting preparation, particularly in the instance where a dental adhesive composition is being formulated.

Preferably, sorbitan monostearate is present in an amount ranging from about 0.5% to about 2.0% by weight of the gel or mobile phase, and more particularly may be present in an amount of from about 0.5% to about 1.5% by weight of the gel or mobile phase.

Sorbitan monostearate is a known emulsifier and surface active agent, and is readily available from a variety of commercial sources.

The present composition may include other additives for a variety of purposes. For example, polyisobutylene may be added in an amount of up to about 10% by weight of the mobile phase, to provide additional softening of the gel for certain applications.

The present compositions may be prepared by heating the primary components preferably with agitation to a temperature sufficient to melt the components, and thereafter homogenizing the melt while cooling it to a temperature at which a uniform and clear, fluid product is obtained. A preferable method of preparation is disclosed in U.S. Pat. No. 3,215,599 to Thau, et al. the pertinent disclosure of which is incorporated herein by reference.

After the mixture of the extrusion aid with the mineral oil and polyethylene wax is complete, and the resulting mixture has been cooled as described above, additional additives may be added under agitation, as desired. Such additives would include various perfumes, emollients, medicaments, colorants and others. The present vehicles or bases are physiologically inert, and are therefore useful both internally as vehicles for carrying medicaments, and externally, in preparing salves, ointments, cosmetic creams and the like.

In a further aspect of the present invention, the present vehicle or mobile phase is a part of a denture adhesive composition characterized by improved extrudability when formulated into a cream or ointment, and dispensed from a tube. The present vehicles or bases are particuarly noteworthy, in that they lend improved extrudability to the adhesive composition without causing a lessening or deterioration of the adhesive properties thereof. In particular, the present vehicles or bases are useful in combination with the adhesive or gum components of the compositions disclosed in U.S. Pat. Nos. 3,003,988, to Germann, et al. and 3,833,518 to Rubin, et al., the disclosures of which are both incorporated herein by reference. The amount of the vehicle or base that may be utilized in such denture adhesives may vary, and particularly may be determined in accordance with the aforementioned patent disclosures. For example, the vehicle or base of the denture adhesives of the present invention may comprise on the order of 50% by weight of the total adhesive composition. Naturally the foregoing percentage is illustrative, and the invention should not be limited thereto.

The present invention will be better understood from a consideration of the following illustrative examples, wherein all percentages are percentages by weight.

EXAMPLES I-VII

A series of vehicles or bases were prepared with varying amounts of sorbitan monostearate, in combination with heavy mineral oil and a polyethylene wax having a molecular weight of approximately 2,000. Of the three components, the polyethylene wax was maintained at a constant content of 13 weight percent, while the amount of heavy mineral oil varied with the amount of sorbitan monostearate, to a maximum of 87 weight percent, in the instance where sorbitan monostearate was deleted entirely.

Each of the bases or vehicles was prepared by heating their respective components and mixing with mild agitation until the polyethylene wax is completely dissolved. Thereafter, the resulting liquid was homogenized and cooled. The respective samples were thereafter tested for viscosity and the results are set forth in Table 1, below.

TABLE I

| EXAMPLE # | % SORBITAN MONOSTEARATE | VISCOSITY (MM cps) |
|---|---|---|
| 1 | 0 | 3.296 (at 20.0° C.) |
| 2 | 0.5 | 2.544 (at 20.0° C.) |
| 3 | 0.8 | 3.232 (at 20.0° C.) |
| 4 | 1.0 | 2.896 (at 20.5° C.) |
| 5 | 1.4 | 2.20 (at 21.5° C.) |
| 6 | 2.5 | 1.824 (at 20.0° C.) |
| 7 | 3.0 | 3.680 (at 20.5° C.) |

In general, the reduction in viscosity evidenced in the samples containing from about 0.5% to about 2.5% of sorbitan monostearate was expected, all but the exception of the viscosity of the preparation of Example 3. Accordingly, these initial viscosities suggested that the corresponding compositions might prove easier to extrude, when incorporated in denture adhesives.

EXAMPLES VIII–XVI

The compositions of Examples 1–8 were combined with the gum phase of a denture adhesive composition, such as that set forth in U.S. Pat. No. 3,833,518. In particular, the mobile phase comprised 50% of the adhesive composition, with the gum phase defined as follows:

| INGREDIENT | WEIGHT PERCENT |
|---|---|
| Methacryloyloxyethyltrimethyl ammonium methyl sulfate | 10% |
| Sodium carboxy-methyl cellulose gum (degree of substitution 0.7) | 36% |
| Sodium carboxy-methyl cellulose gum (degree of substitution 0.4) | 4% |
| F.D. & C. #3 aluminum lake | (about .01%) |

The gum phase was mixed dry until complete blending was achieved. Thereafter, the individual mobile phases of the previous examples were combined with equal amounts of the gum phase to form the respective denture adhesives. The resulting adhesive compositions were then tested for viscosity and extrudability. The extrudability was measured by placing each of the adhesive samples in individual 1.5 ounce tubes having identical orifices. Each tube was then placed under 20 PSI pressure for 5 seconds, and the quantity of adhesive extruded out of the tube was then weighed and tabulated. The results of the various tests of the dental compositions, including viscosity and quantity of composition extruded, are set forth in Table II, below.

TABLE II

| DENTURE ADHESIVE COMPOSITIONS | | | | |
|---|---|---|---|---|
| EXAMPLE NO. | EXAMPLE NO. OF MOBILE PHASE | AMOUNT OF SORBITAN MONOSTEARATE (WEIGHT %) | VISCOSITY (MM cps) | AMOUNT EXTRUDED (GRAMS) |
| 8* | 1 | 0 | 2.20 (@ 20.0° C.) | 4.303 |
| 9* | 1 | 0 | 2.56 (@ 20.0° C.) | 4.198 |
| 10 | 2 | 0.5 | 1.856 (@ 20.0° C.) | 5.350 |
| 11 | 3 | 0.8 | 1.680 (@ 20.0° C.) | 5.256** |
| 12 | 4 | 1.0 | 1.632 (@ 20.5° C.) | 5.70 |
| 13 | 5 | 1.4 | 1.50 (@ 21.5° C.) | 4.81 |
| 14* | 6 | 2.5 | 1.760 (@ 20.5° C.) | 3.87 |
| 15* | 6 | 2.5 | 1.664 (@ 20.5° C.) | 4.103 |
| 16 | 7 | 3.0 | 3.680 (@ 20.5° C.) | 3.762 |

*two adhesives identical in composition test and results for both recorded.
**average of two runs of 4.952 grams and 5.560 grams, respectively.

From the above results, it is apparent that those preparations, particularly the adhesives of Examples 10–13, exhibited improved extrudability over the remaining samples tested. It is thus apparent that the presence of sorbitan monostearate within a specific defined range positively contributes to improved extrudability, while amounts of sorbitan monostearate falling outside that range exerts no positive effect, and, in the instance of additional quantities of the extrusion aid, may decrease the extrudability of the resulting adhesive composition.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. In an improved denture adhesive composition comprising an adhesive component and a vehicle, wherein said vehicle comprises a gel consisting essentially of:
   A. a mineral oil component;
   B. a polyolefin wax component; the improvement wherein said vehicle comprises
      sorbitan monostearate, in an amount of from about 0.25% to about 2.25% by weight of said gel wherein said denture adhesive exhibits improved extrudability.

2. The denture adhesive of claim 1 wherein sorbitan monostearate is present in an amount of from about 0.5% to about 2.0% by weight of said gel.

3. The denture adhesive of claim 1 wherein said sorbitan monostearate is present in an amount of from about 0.5% to about 1.5% by weight of said gel.

4. The denture adhesive of claims 1, 2 or 3 wherein said polyethylene wax has a molecular weight ranging from about 1,000 to about 3,000.

5. The denture adhesive of claim 4 wherein said polyethylene wax has a molecular weight of 2,000.

6. The denture adhesive of claims 1, 2 or 3 wherein said polyolefin wax is present in an amount ranging from about 5% to about 25% by weight of said gel.

7. The denture adhesive of claim 6 wherein said polyolefin wax is present in an amount ranging from about 10% to about 20% by weight of said gel.

8. The denture adhesive of claim 7 wherein said polyolefin wax is present in an amount of from about 11% to about 17% by weight of said gel.

9. The denture adhesive of claims 1, 2 or 3 wherein said mineral oil is present in an amount ranging from about 75% to about 95% by weight of said gel.

10. The denture adhesive of claim 9 wherein said mineral oil is present in an amount ranging from about 80% to about 90% by weight of said gel.

11. The denture adhesive of claim 10 wherein said mineral oil is present in an amount ranging from about 83% to about 89% by weight of said gel.

12. The denture adhesive of claim 6 wherein said mineral oil is present in an amount ranging from about 75% to about 95% by weight of said gel.

13. The denture adhesive of claim 7 wherein said mineral oil is present in an amount ranging from about 80% to about 90% by weight of said gel.

14. The denture adhesive of claim 8 wherein said mineral oil is present in an amount ranging from about 83% to about 89% by weight of said gel.

15. The denture adhesive of claims 1, 2 or 3 further including up to about 10% by weight based on said gel, of a softener comprising polyisobutylene.

16. The denture adhesive of claim 1, 2 or 3 further including up to about 10% by weight based on said gel, of a softener comprising polyisobutylene.

17. The denture adhesive of claim 6 further including up to about 10% by weight based on said gel, of a softener comprising polyisobutylene.

18. The denture adhesive of claim 9 further including up to about 10% by weight based on said gel, of a softener comprising polyisobutylene.

19. An improved vehicle useful for denture adhesive compositions, said vehicle comprising a gel consisting essentially of:
  A. a mineral oil component;
  B. a polyolefin wax component; the improvement wherein said vehicle comprises
    sorbitan monostearate, in an amount of from about 0.25% to about 2.25% by weight of said gel wherein said denture adhesive exhibits improved extrudability.

20. The vehicle of claim 19 wherein sorbitan monostearate is present in an amount of from about 0.5% to about 2.0% by weight of said gel.

21. The vehicle of claim 20 wherein said sorbitan monostearate is present in an amount of from about 0.5% to about 1.5% by weight of said gel.

22. The vehicle of claims 19, 20 or 21 wherein said polyethylene wax has a molecular weight ranging from about 1,000 to about 3,000.

23. The vehicle of claim 22 wherein said polyethylene wax has a molecular weight of 2,000.

24. The vehicle of claims 19, 20 or 21 wherein said polyolefin wax is present in an amount ranging from about 5% to about 25% by weight of said gel.

25. The vehicle of claim 24 whereifn said polyolefin wax is present in an amount ranging from about 10% to about 20% by weight of said gel.

26. The vehicle of claim 25 wherein said polyolefin wax is present in an amount of from about 11% to about 17% by weight of said gel.

27. The vehicle of claims 19, 20 or 21 wherein said mineral oil is present in an amount ranging from about 75% to about 95% by weight of said gel.

28. The vehicle of claim 27 wherein said mineral oil is present in an amount ranging from about 80% to about 90% by weight of said gel.

29. The vehicle of claim 28 wherein said mineral oil is present in an amount ranging from about 83% to about 89% by weight of said gel.

30. The vehicle of claim 24 wherein said mineral oil is present in an amount ranging from about 75% to about 95% by weight of said gel.

31. The vehicle of claim 25 wherein said mineral oil is present in an amount ranging from about 80% to about 90% by weight of said gel.

32. The vehicle of claim 26 wherein said mineral oil is present in an amount ranging from about 83% to about 89% by weight of said gel.

33. The vehicle of claims 19, 20 or 21 further including up to about 10% by weight based on said gel, of a softener comprising polyisobutylene.

34. The vehicle of claim 24 further including up to about 10% by weight based on said gel, of a softener comprising polyisobutylene.

35. The vehicle of claim 27 further including up to about 10% by weight based on said gel, of a softener comprising polyisobutylene.

* * * * *